United States Patent
Akaki et al.

(10) Patent No.: US 7,883,467 B2
(45) Date of Patent: Feb. 8, 2011

(54) ULTRASONIC DIAGNOSTIC APPARATUS

(75) Inventors: Kazuya Akaki, Nasushiobara (JP); Hidesuke Tomura, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 290 days.

(21) Appl. No.: 11/251,883

(22) Filed: Oct. 18, 2005

(65) Prior Publication Data

US 2006/0084871 A1  Apr. 20, 2006

(30) Foreign Application Priority Data

Oct. 19, 2004 (JP) ............... 2004-304505

(51) Int. Cl.
*A61B 8/00* (2006.01)

(52) U.S. Cl. ..................... 600/443; 600/437

(58) Field of Classification Search ............... 600/407, 600/437, 443

See application file for complete search history.

(56) References Cited

U.S. PATENT DOCUMENTS

| | | | |
|---|---|---|---|
| 5,099,847 A | 3/1992 | Powers et al. | |
| 5,920,317 A * | 7/1999 | McDonald | 715/853 |
| 6,213,944 B1 * | 4/2001 | Miller et al. | 600/437 |
| 6,436,040 B1 * | 8/2002 | Collamore et al. | 600/437 |
| 6,447,450 B1 * | 9/2002 | Olstad | 600/437 |
| 6,480,186 B1 * | 11/2002 | McCabe et al. | 345/168 |
| 2003/0013959 A1 * | 1/2003 | Grunwald et al. | 600/437 |
| 2004/0066389 A1 * | 4/2004 | Skyba et al. | 345/619 |
| 2005/0124893 A1 * | 6/2005 | Ohtake et al. | 600/450 |

* cited by examiner

*Primary Examiner*—Brian Casler
*Assistant Examiner*—Peter Luong
(74) *Attorney, Agent, or Firm*—Oblon, Spivak, McClelland, Maier & Neustadt, L.L.P.

(57) ABSTRACT

An event signal is generated in response to a specific event as a trigger. A recording control unit controls the operation of an image recording unit on the basis of the event signal, thereby automatically forming, as a unit, and recording moving image information based on a unified standard. In addition, an event signal is generated in response to a specific event as a trigger. On the basis of ultrasonic image data of a frame corresponding to the event signal generation, a representative image as an index for search is automatically generated and recorded in association with the ultrasonic image data of the corresponding frame. Furthermore, the recorded representative image is read out and set on the screen. The ultrasonic image data is reproduced on the basis of the frame associated with the representative image selected by the operator.

14 Claims, 14 Drawing Sheets

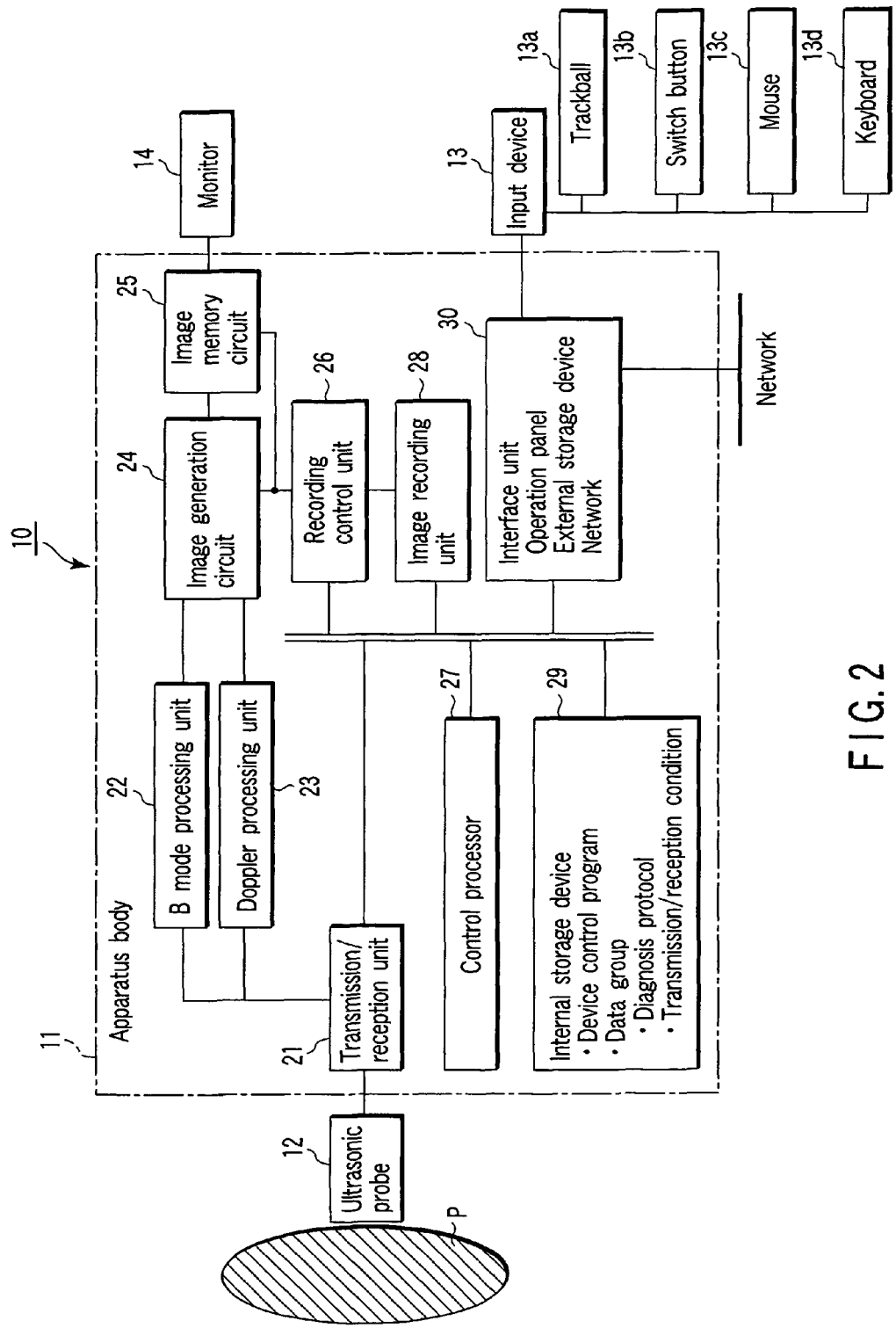
F I G. 2

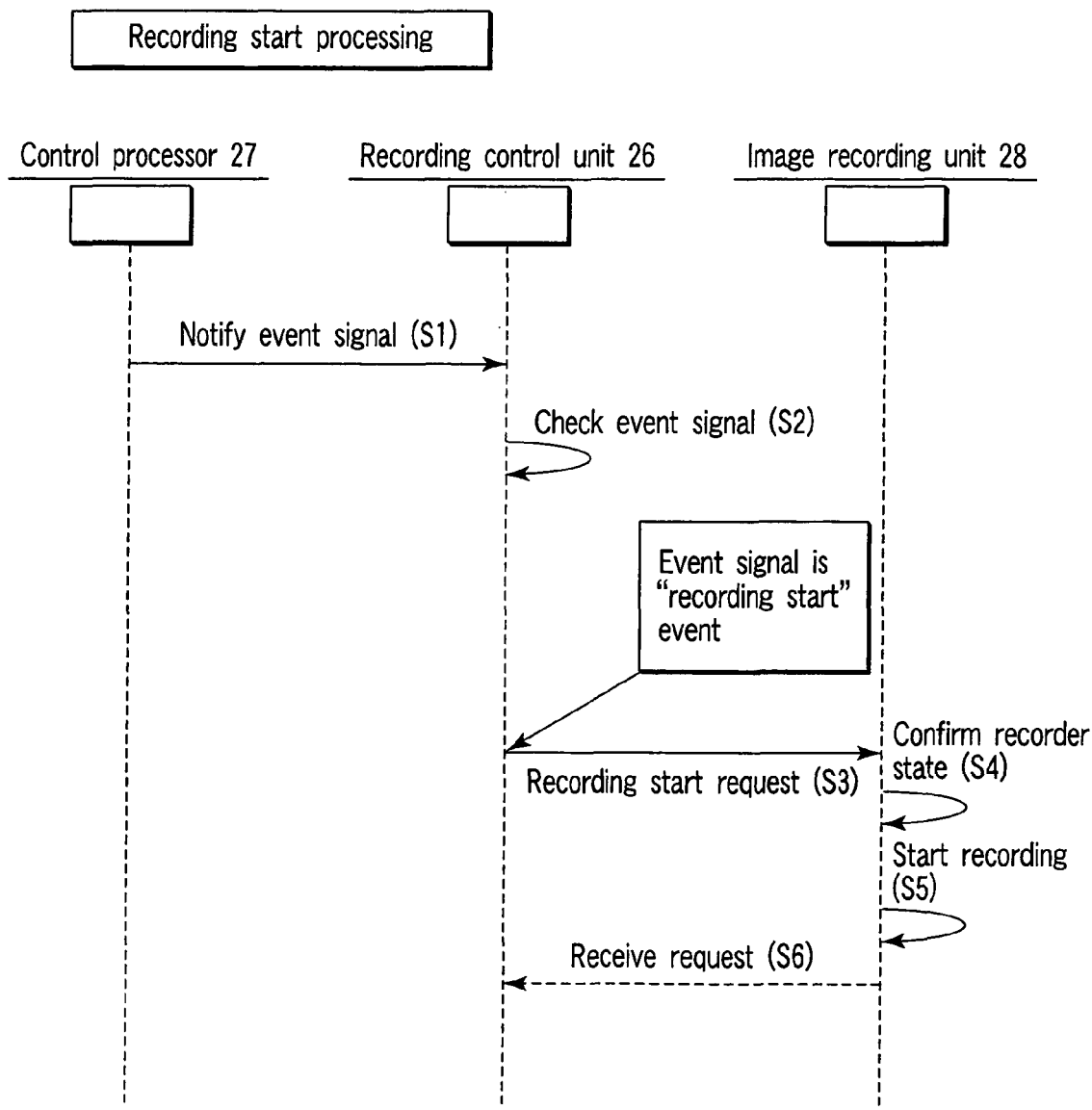
F I G. 3A

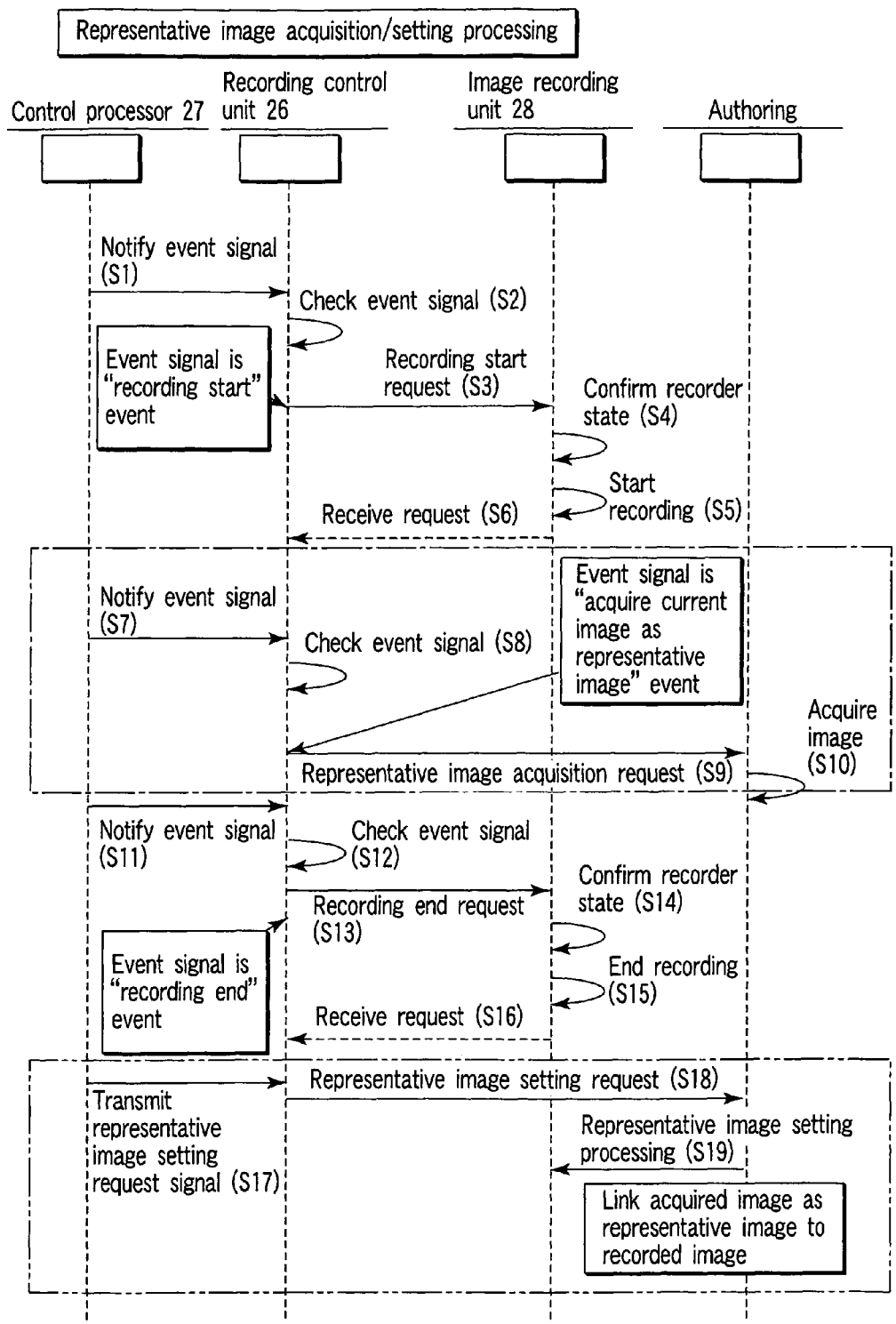
F I G. 12

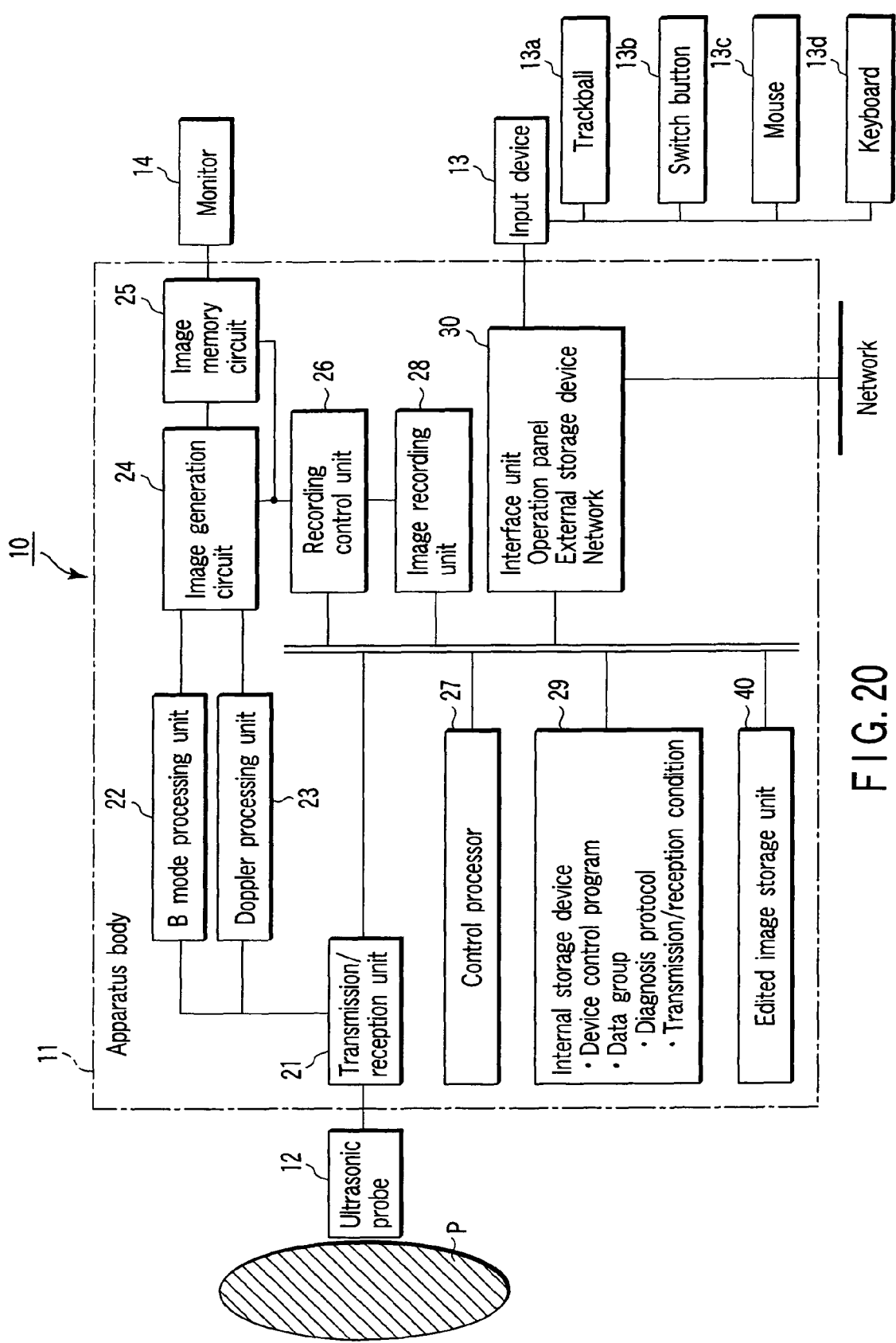
F I G. 20

US 7,883,467 B2

ULTRASONIC DIAGNOSTIC APPARATUS

CROSS-REFERENCE TO RELATED APPLICATIONS

This application is based upon and claims the benefit of priority from prior Japanese Patent Application No. 2004-304505, filed Oct. 19, 2004, the entire contents of which are incorporated herein by reference.

BACKGROUND OF THE INVENTION

1. Field of the Invention

The present invention relates to an ultrasonic diagnostic apparatus which is highly operable and efficient in recording an obtained ultrasonic image or searching for a recorded ultrasonic image.

2. Description of the Related Art

An ultrasonic diagnostic apparatus is a diagnostic apparatus for displaying an image of in vivo information. The ultrasonic diagnostic apparatus is less expensive and causes no exposure, as compared to other image diagnostic apparatuses such as an X-ray diagnostic apparatus or an X-ray computerized topographic apparatus, and is useful for noninvasive observation in real time. The ultrasonic diagnostic apparatus has a wide application range because of its characteristics and is used to diagnose circulatory organs such as a heart, abdominal organs such as a liver and kidney, peripheral vessels, cerebral blood vessels or in diagnosis in obstetrics and gynecology.

Generally, in imaging using an ultrasonic diagnostic apparatus, not only a still image but also a moving image in a predetermined period must be acquired and saved at a timing unique to the subject or the imaging method. To do this, a conventional ultrasonic diagnostic apparatus saves a moving image in a total imaging time from the start to end of examination, as shown in FIG. 1A, or a moving image corresponding to a predetermined period by causing the operator to start and stop recording, as shown in FIG. 1B.

BRIEF SUMMARY OF THE INVENTION

However, the conventional moving image saving methods have, e.g., the following problems.

When the method of recording all images during examination is employed, even images unnecessary for diagnosis are also saved. Hence, areas of recording media are wasted. When the method of recording images in accordance with the recording start/stop operation executed by the operator during imaging is employed, the operator may forget the start or end of recording. Hence, images may be missed, or unnecessary images may be recorded.

In either method, to call up necessary scenes (still images and moving images) from the saved moving images, unnecessary images must also be browsed. This makes the image search operation inefficient and increases the load on the observer.

Even the VHS index search system (VISS) function of a VCR or file division of an HDD or DVD recorder allows search based on the recording/stop operation. In this case, however, the observer still needs to search for a desired scene by checking recorded images while fast-forwarding them.

The present invention has been made in consideration of the above situation, and has as its object to provide an ultrasonic diagnostic apparatus capable of recording images while excluding those unnecessary for diagnosis as much as possible and executing image search with excellent operability and high efficiency.

According to an aspect of the present invention, there is provided an ultrasonic diagnostic apparatus comprising an ultrasonic probe which transmits an ultrasonic wave to a predetermined part of a subject and receives an echo signal from the predetermined part, a driving signal generation unit which generates a driving signal to drive the ultrasonic probe and supplies the driving signal to the ultrasonic probe, an image data generation unit which generates ultrasonic image data of a plurality to frames on the basis of the echo signal received by the ultrasonic probe, a recording unit which records the ultrasonic image data of each frame, a signal generation unit which generates an event signal in response to a predetermined event as a trigger, and a control unit which controls at least one of a start and an end of recording of the ultrasonic image data by the recording unit in response to the event signal.

According to another aspect of the present invention, there is provided an ultrasonic diagnostic apparatus comprising an ultrasonic probe which transmits an ultrasonic wave to a predetermined part of a subject and receives an echo signal from the predetermined part, a driving signal generation unit which generates a driving signal to drive the ultrasonic probe and supplies the driving signal to the ultrasonic probe, an image data generation unit which generates ultrasonic image data of a plurality to frames on the basis of the echo signal received by the ultrasonic probe, a signal generation unit which generates an event signal in response to a predetermined event as a trigger, a representative image generation unit which generates a representative image symbolically representing an ultrasonic image corresponding to the echo signal received in a period before or after event signal generation on the basis of the ultrasonic image data of a frame corresponding to the event signal generation timing, a recording unit which records the ultrasonic image data of the plurality of frames and also records the representative image in association with the ultrasonic image data of the corresponding frame, and an image reproduction unit which, when the representative image is selected, reproduces the ultrasonic image data on the basis of the frame associated with the selected representative image.

According to still another aspect of the present invention, there is provided an ultrasonic diagnostic apparatus comprising an ultrasonic probe which transmits an ultrasonic wave to a predetermined part of a subject and receives an echo signal from the predetermined part, a driving signal generation unit which generates a driving signal to drive the ultrasonic probe and supplies the driving signal to the ultrasonic probe, an image data generation unit which generates ultrasonic image data of a plurality to frames on the basis of the echo signal received by the ultrasonic probe, a signal generation unit which generates at least one of a first event signal to instruct one of a start and an end of image recording and a second event signal to instruct representative image acquisition in response to a predetermined event as a trigger, a control unit which controls one of the start and the end of recording of the ultrasonic image data in response to the first event signal, a representative image generation unit which generates a representative image symbolically representing an ultrasonic image corresponding to the echo signal received in a period before or after event signal generation on the basis of the ultrasonic image data of a frame corresponding to the second event signal generation timing, a recording unit which records the ultrasonic image data of the plurality of frames and also records the representative image in association with the ultrasonic image data of the corresponding frame under control of the control unit, and an image reproduction unit which, when the representative image is selected, reproduces the ultrasonic image data on the basis of the frame associated with the selected representative image.

According to still another aspect of the present invention, there is provided an ultrasonic diagnostic apparatus comprising an image data generation unit which transmits an ultrasonic wave to a predetermined part of a subject and generates ultrasonic image data of a plurality to frames on the basis of an echo signal received from the predetermined part, a signal generation unit which generates an event signal in response to a predetermined event as a trigger, a recording unit which records the ultrasonic image data of each frame together with event information containing a type and generation timing of the event signal, and an editing unit which edits the ultrasonic image data of the plurality of frames on the basis of the event information.

BRIEF DESCRIPTION OF THE SEVERAL VIEWS OF THE DRAWING

FIG. 2 is a block diagram for explaining the arrangement of an ultrasonic diagnostic apparatus 10 according to the first embodiment;

FIG. 3A is a view for explaining recording start processing by the image recording function of the ultrasonic diagnostic apparatus 10;

FIG. 12 is a view for explaining processing by the representative image acquisition/setting function of the ultrasonic diagnostic apparatus 10;

FIG. 20 is a block diagram for explaining the arrangement of an ultrasonic diagnostic apparatus 10 according to the second embodiment.

DETAILED DESCRIPTION OF THE INVENTION

Figure 1A:
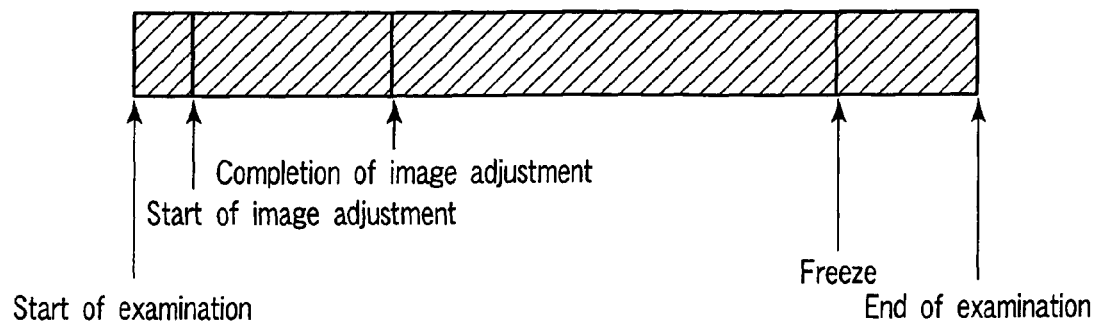
FIG. 1A is a view for explaining the image recording method of a conventional ultrasonic diagnostic apparatus.
Figure 1B:
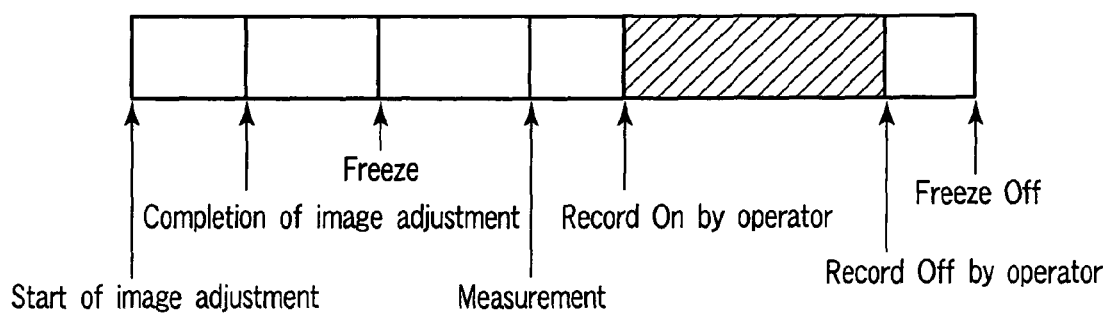
FIG. 1B is a view for explaining the image recording method of another conventional ultrasonic diagnostic apparatus.

The first and second embodiments of the present invention will be described below with reference to the accompanying drawing. In the following description, the same reference numerals denote constituent elements having almost the same function and arrangement, and a repetitive description will be done only when necessary.

First Embodiment

FIG. 2 is a block diagram of an ultrasonic diagnostic apparatus 10 according to this embodiment. As shown in FIG. 2, the ultrasonic diagnostic apparatus 10 includes an ultrasonic probe 12, an apparatus body 11, an external input device 13 which is connected to the apparatus body 11 to input various kinds of instructions, commands, and information from an operator to the apparatus body 11, and a monitor 14. The input device 13 includes a trackball 13a, switch button 13b, mouse 13c, and keyboard 13d to, e.g., set a region of interest (ROI).

The ultrasonic probe 12 has piezoelectric vibrators each serving as an acoustoelectric reversible conversion element of, e.g., piezoelectric ceramics. The plurality of piezoelectric vibrators are juxtaposed and provided at the tip of the probe 12.

The apparatus body 11 has an ultrasonic transmission/reception unit 21, B mode processing unit 22, Doppler processing unit 23, image generation circuit 24, image memory circuit 25, recording control unit 26, control processor (CPU) 27, image recording unit 28, internal storage device 29, and interface unit 30.

The ultrasonic transmission/reception unit 21 reads out transmission/reception conditions which are stored in the internal storage device 29 by the control processor 27 and generates rate pulses in accordance with the transmission/reception conditions. The ultrasonic transmission/reception unit 21 gives, to each rate pulse, a delay time necessary for converging an ultrasonic wave into a beam and determining the transmission directivity and applies a voltage pulse to the probe 12 for each channel. The probe 12 transmits an ultrasonic beam to a subject.

For a circulatory organ, to collect images by a specific cardiac time phase, an ECG-gated unit is connected to the apparatus body 11. An electrocardiographic signal of a patient is input through the ECG-gated unit. For this electrocardiographic signal, information about display or image collection timing is input from the operation panel. The control processor 27 controls the image collection timing of the transmission/reception unit 21 on the basis of the electrocardiographic signal and information. The electrocardiographic signal is stored in the image recording unit 28 or external storage device and combined with another image information or additional information such as character information by the image memory circuit 25.

In addition, on the basis of mode selection, ROI setting, or transmission start/end input by the user through the input device 13 or another interface, the transmission/reception conditions and device control program stored in the internal storage device 29 are read out. In accordance with them, the control processor 27 controls the transmission/reception unit 21.

The ultrasonic beam sent into the subject to generate an image is reflected by the discontinuity surface of acoustic impedance in the subject. The reflected wave is received by the probe 12. An echo signal output from the probe 12 for each channel is received by the transmission/reception unit 21. The echo signal is amplified for each channel, given a delay time necessary for determining the reception directivity, and added in the transmission/reception unit 21. By this addition, a reflection component from a direction corresponding to the reception directivity is enhanced. The total directivity of ultrasonic transmission/reception is determined by the transmission directivity and reception directivity. This directivity is generally called a "scan line".

The echo signal output from the transmission/reception unit 21 is sent to the B mode processing unit 22 and Doppler processing unit 23. The B mode processing unit 22 includes a logarithmic converter, envelop detection circuit, and analog-to-digital (A/D) converter, although they are not illustrated. The logarithmic converter logarithmically converts the echo signal. The envelop detection circuit detects the envelop of the output signal from the logarithmic converter. The detection signal is digitized through the analog-to-digital converter and output as detection data. The Doppler processing unit 23 extracts a blood flow component by using a result of frequency analysis or a filter and obtains blood information such as mean velocities, variances, powers, and the like at multiple points.

The image generation circuit 24 executes frame correlation processing by using the detection data input from the B mode processing unit 22 to generate a B mode image. The image generation circuit 24 also creates a mean velocity image, variance image, power image, and combined image thereof by using the blood flow information input from the Doppler processing unit 23.

The image memory circuit 25 generates an ultrasonic image to be displayed on the monitor 14 on the basis of the image data (also called "raw data") received from the image generation circuit 24. The image memory circuit 25 includes a scan converter, cinememory, frame memory, and video converter. The scan converter converts a scan line signal sequence of ultrasonic scan, which is input from the image generation circuit 24, into data of an orthogonal coordinate system based on spatial information. The cinememory saves, e.g., ultrasonic images corresponding to a plurality of frames immediately before freeze. When images stored in the cinememory are continuously displayed (cinedisplayed), an ultrasonic moving image can be displayed. The frame memory stores an ultrasonic image of one frame. An image currently stored in the frame memory is displayed on the monitor 14. An overwrite in the frame memory is stopped by, e.g., pressing the freeze ON button of the operation input device 13. The video converter executes video format conversion of image data received from the frame memory.

The recording control unit 26 checks an event signal received from the control processor 27. If the event signal is related to a recording start/recording end event (representative image acquisition event), the image recording start/recording end timing (representative image acquisition timing) of the image recording unit 28 is controlled on the basis of the event signal.

The control processor 27 executes programs stored in the image recording unit 28 or external storage device and read out from the internal storage device 29 on the basis of information input from various kinds of switches or trackball 13a.

The control processor 27 also executes processing by an image recording function or representative image acquisition/setting function (to be described later) in accordance with a predetermined program stored in, e.g., the internal storage device 29.

The image recording unit 28 records a still image or moving image under the control of the recording control unit 26. The image recording unit 28 also forms and records units of moving images in each period, which are recorded by a series of imaging sequences, under the control of the recording control unit 26. The image recording unit 28 also stores a representative image (to be described later) in association with a corresponding frame image.

The internal storage device 29 stores the control program of the apparatus, diagnostic protocols, various kinds of data such as transmission/reception conditions, and collected image data. The internal storage device 29 also stores various kinds of subprograms (activities) to implement each processing of a series of examination procedures and a control program to control the apparatus in accordance with the examination procedures (work flow) including the various kinds of activities.

The monitor 14 displays, as an image, morphologic information or blood flow information in a living body on the basis of the video signal from the image memory circuit 25. An image displayed on the monitor 14 is recorded in, e.g., the image recording unit 28 by using corresponding image data stored in the frame memory in the image memory circuit 25.

(Image Recording Function)

The image recording function of the ultrasonic diagnostic apparatus 10 will be described next. In this function, an event signal is generated by using a specific event as a trigger under the control of the control processor 27. On the basis of the event signal, the recording control unit 26 controls the storage operation (recording start/recording end) of the image recording unit 28, thereby automatically forming and recording units of moving image information based on a unified standard.

Recording start processing by the image recording function will be described. FIG. 3A is a view for explaining recording start processing. As shown in FIG. 3A, in response to a predetermined event as a trigger, the control processor 27 generates an event signal to give a notification of generation of the event and its type and transmits the event signal to the recording control unit 26 (step S1). The recording control unit 26 checks the event signal received from the control processor 27 (step S2). If it is determined that the event signal instructs the start of image recording, the recording control unit 26 requests the image recording unit 28 to start recording (step S3). The image recording unit 28 confirms the state (recorder state) of its own (step S4). If the image recording unit 28 is in a recordable state, recording is started (step S5). The image recording unit 28 transmits, to the recording control unit 26, a signal to indicate that the recording start request is received (step S6). In response to this indication, image data of each frame is sent from the image memory circuit 25 to the image recording unit 28 through the recording control unit 26.

Figure 3B:
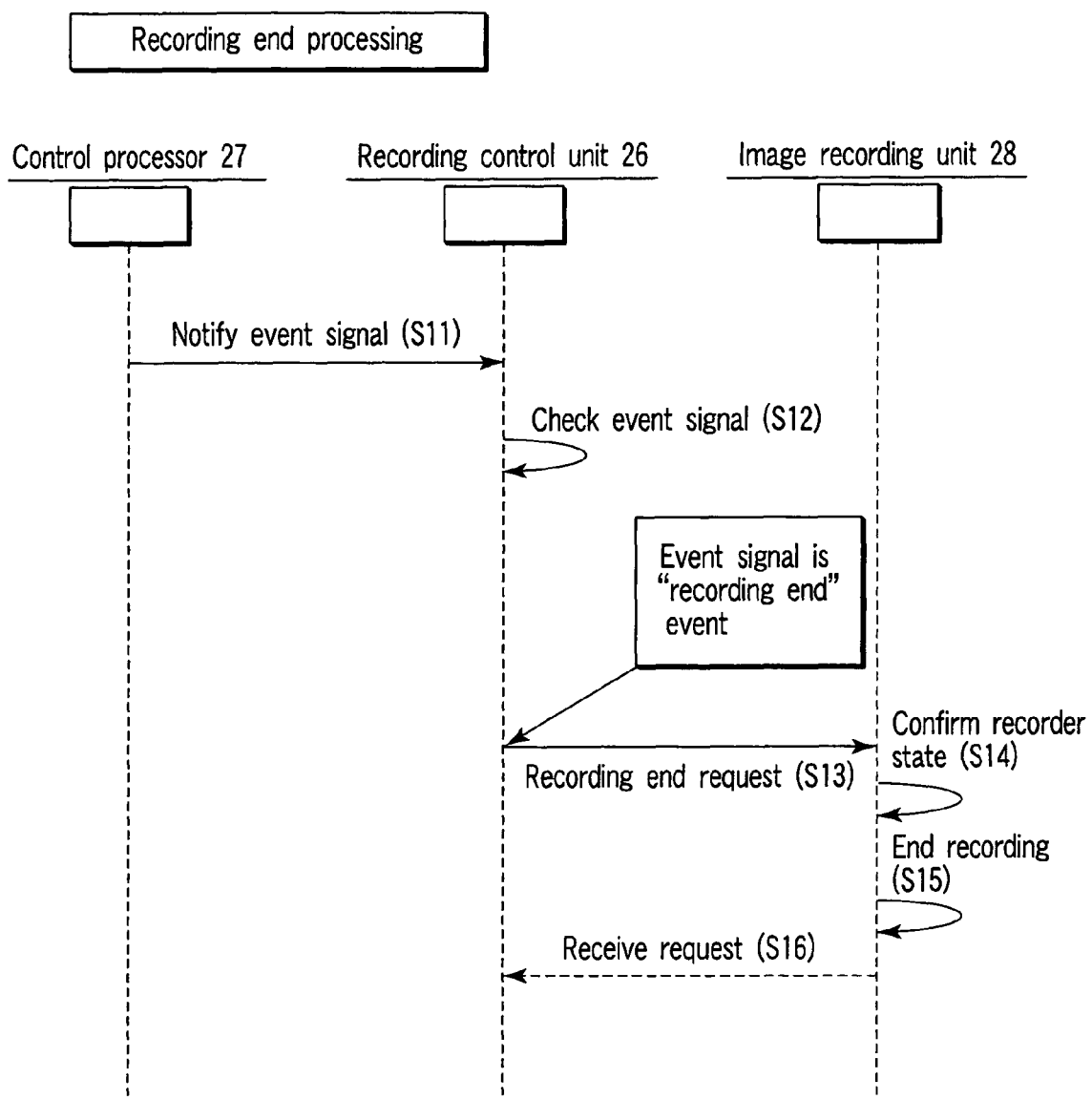
FIG. 3B is a view for explaining recording end processing by the image recording function of the ultrasonic diagnostic apparatus 10.

Recording end processing by the image recording function will be described next. FIG. 3B is a view for explaining recording end processing. As shown in FIG. 3B, almost the same processing as in recording start processing is executed in the recording end processing. That is, in response to a predetermined event as a trigger, the control processor 27 generates an event signal to give a notification of generation of the event and its type and transmits the event signal to the recording control unit 26 (step S11). The recording control unit 26 checks the event signal received from the control processor 27 (step S12). If it is determined that the event signal instructs the end of image recording, the recording control unit 26 requests the image recording unit 28 to end recording (step S13). The image recording unit 28 confirms the state (recorder state) of its own (step S14). If the image recording unit 28 is in a recordable state, recording is ended (step S15). The image recording unit 28 transmits, to the recording control unit 26, a signal to indicate that the recording end request is received (step S16), and image recording is ended.

The contents of predetermined events serving as a trigger in steps S1 and S11 are not particularly limited. Detailed examples are an input operation unique to ultrasonic diagnosis (e.g., image adjustment operation, freeze ON/OFF operation, predetermined measurement operation, annotation operation, still image saving operation, or ultrasonic image print operation) and device operations (e.g., detection of a change in image layout on the display screen to display an ultrasonic image or a change by a predetermined threshold value or more in luminance of ultrasonic image data of each frame generated by the image data generation unit). Which input operation or device operation should be used as the recording start (end) event is preferably arbitrarily registered. With this arrangement, the operator can start (end) moving image recording by using a desired input operation or the like as a trigger.

Examples of the image recording function of the ultrasonic diagnostic apparatus 10 will be described below by exemplifying an input operation or device operation used as the recording start/recording end event. When digital imaging and communications in medicine (DICOM) is used as an image communication standard, each recording start/recording end event is recorded as group information of a DICOM tab. The operator can also search for desired image data by using the recording start/recording end event as an index.

Example 1

In this example, the image recording start event is the final image adjustment operation, and the image recording end event is the operation of a freeze ON button.

Figure 4:
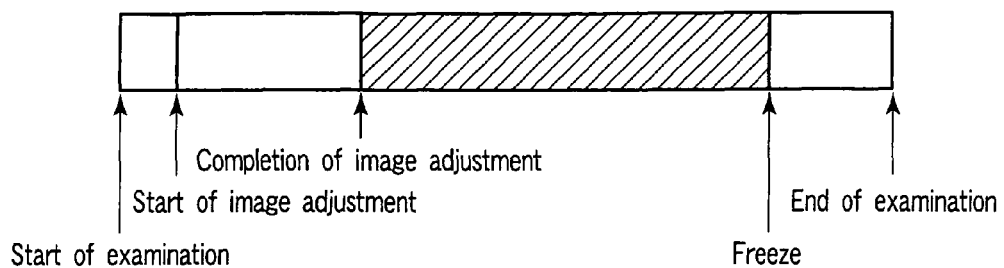
FIG. 4 is a view for explaining Example 1 of the ultrasonic diagnostic apparatus, in which the image recording start event is the final image adjustment operation, and the image recording end event is the operation of a freeze button.

FIG. 4 is a view for explaining Example 1 of the ultrasonic diagnostic apparatus. As shown in FIG. 4, in this example, image recording is not started even at the examination start timing. When the operator starts image adjustment while observing the monitor 14 and completes image adjustment by the final operation, image recording is triggered by this final operation. Whether the operation executed by the operator is the final image adjustment operation is determined in the following way. For example, of four image adjustment buttons including freeze OFF, image mode transition, scale change, and gain adjustment, input of the button finally operated (i.e., 4/4th determination) is determined as the image recording start event. In response to this event, an event signal to instruct the start of image recording is generated.

To execute image adjustment again after input of the image adjustment button operated finally, precedingly recorded moving image data can be erased by executing a predetermined reset operation.

When moving image recording starts in response to the final image adjustment operation, image data corresponding to the period until the operator operates the freeze ON button is formed as a unit and recorded in the image recording unit 28 as a series of moving image data.

Example 2

In this example, the image recording start event is the operation of causing the operator to execute predetermined measurement, and the image recording end event is the operation of a freeze OFF button.

Figure 5:
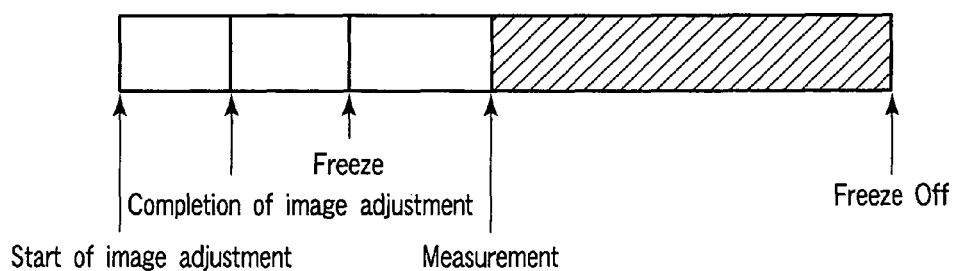
FIG. 5 is a view for explaining Example 2 of the ultrasonic diagnostic apparatus, in which the image recording start event is the operation of causing the operator to execute predetermined measurement, and the image recording end event is the operation of a freeze OFF button.

FIG. 5 is a view for explaining Example 2 of the ultrasonic diagnostic apparatus. As shown in FIG. 5, in this example, image recording is not started even at the completion of image adjustment or at the freeze ON switch operation timing. Image recording is triggered by a button operation of causing the operator to execute measurement by using an ultrasonic image displayed on the monitor 14. Which measurement (e.g., geometrical measurement to measure, e.g., a distance or luminance change measurement by TIC creation) instructed by a button operation should be used as the recording start event can be registered in advance. In this example, when a button operation of instructing TIC creation is registered as the recording start event, the control processor 27 generates an event signal to instruct the start of image recording in response to the button operation.

To execute a plurality of (e.g., n) measurements, for example, the final operation of the measurement execution button (i.e., n/nth determination) may be determined as the image recording start event.

When moving image recording starts in response to the operation of the measurement execution button, image data corresponding to the period until the operator operates the freeze OFF button is formed as a unit and recorded in the image recording unit 28 as a series of moving image data.

Example 3

Figure 6:
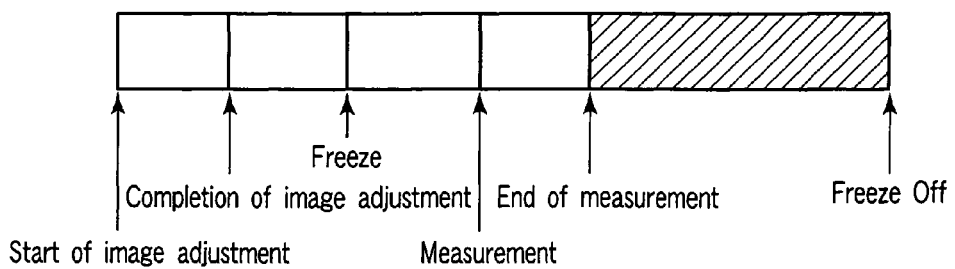
FIG. 6 is a view for explaining Example 3 of the ultrasonic diagnostic apparatus, in which the image recording start event is the end instruction operation of measurement using an ultrasonic image, and the image recording end event is the operation of the freeze OFF button.

FIG. 6 is a view for explaining Example 3 of the ultrasonic diagnostic apparatus. In this example, the image recording start event is the end instruction operation of measurement using an ultrasonic image, and the image recording end event is the operation of the freeze OFF button. Which measurement (e.g., geometrical measurement to measure, e.g., a distance or luminance change measurement by TIC creation) whose end is instructed by a button operation should be used as the recording start event can be registered in advance. In this example, when a button operation of instructing the end of TIC creation is registered as the recording start event, the control processor 27 generates an event signal to instruct the start of image recording in response to the button operation.

To execute a plurality of (e.g., n) measurements, for example, the final operation of the measurement end button (i.e., n/nth determination) may be determined as the image recording start event.

When moving image recording starts in response to the operation of the measurement end button, image data corresponding to the period until the operator operates the freeze OFF button is formed as a unit and recorded in the image recording unit 28 as a series of moving image data.

Example 4

Figure 7:
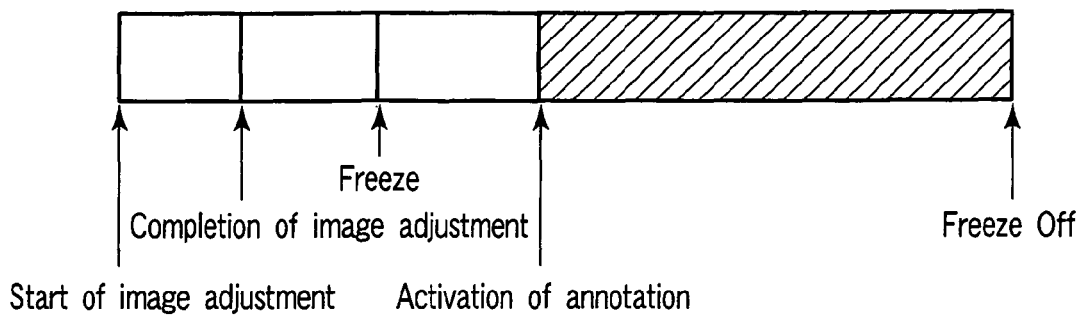
FIG. 7 is a view for explaining Example 4 of the ultrasonic diagnostic apparatus, in which the image recording start event is activation of an annotation function, and the image recording end event is the operation of the freeze button.

FIG. 7 is a view for explaining Example 4 of the ultrasonic diagnostic apparatus. In this example, the image recording start event is activation of an annotation function, and the image recording end event is the operation of the freeze button.

An image to which an annotation is input by the annotation function is effective for diagnosis at a high probability. Hence, in this example, ultrasonic images after activation of the annotation function are recorded, thereby forming and recording units of moving images during the period from the frame image as the annotation input target to the freeze OFF operation in the image recording unit 28 as a series of moving image data.

Example 5

In this example, the image recording start event is a completion instruction of annotation input by the annotation function, and the image recording end event is the operation of the freeze button.

Figure 8:
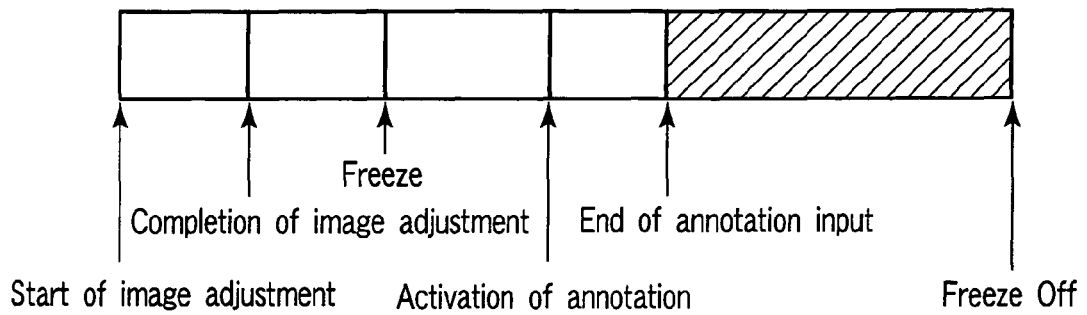
FIG. 8 is a view for explaining Example 5 of the ultrasonic diagnostic apparatus, in which the image recording start event is a completion instruction of annotation input by the annotation function, and the image recording end event is the operation of the freeze button.

FIG. 8 is a view for explaining Example 5 of the ultrasonic diagnostic apparatus. As in Example 4, an image to which an annotation is input by the annotation function is effective for diagnosis at a high probability. Hence, in this example, moving images during the period from the frame image in which annotation input by the annotation function is completed to the freeze OFF operation are formed as units and recorded in the image recording unit 28 as a series of moving image data.

Example 6

Figure 9:
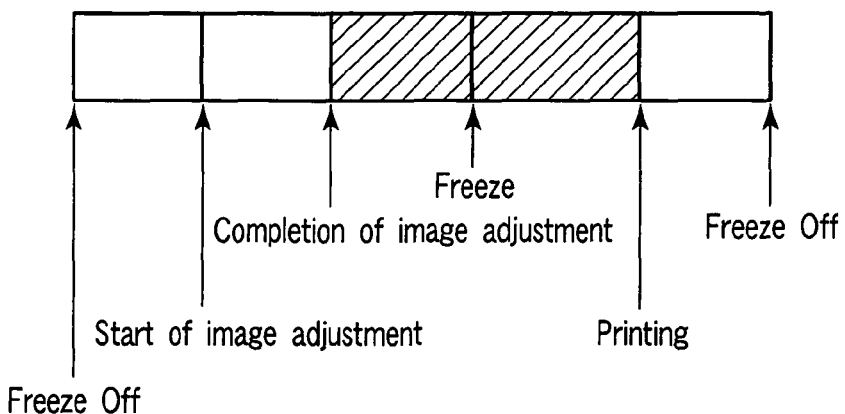
FIG. 9 is a view for explaining Example 6 of the ultrasonic diagnostic apparatus, in which the image recording start event is the final image adjustment operation, and the image recording end event is a print instruction operation.

FIG. 9 is a view for explaining Example 6 of the ultrasonic diagnostic apparatus. In this example, the image recording start event is the final image adjustment operation, and the image recording end event is a print instruction operation.

More specifically, an ultrasonic image output by printing is effective for diagnosis at a high probability. Hence, in this example, moving images during the period from a predetermined recording start event (final image adjustment operation in this example) to the print instruction are formed as units and recorded in the image recording unit 28 as a series of moving image data.

Example 7

Figure 10:
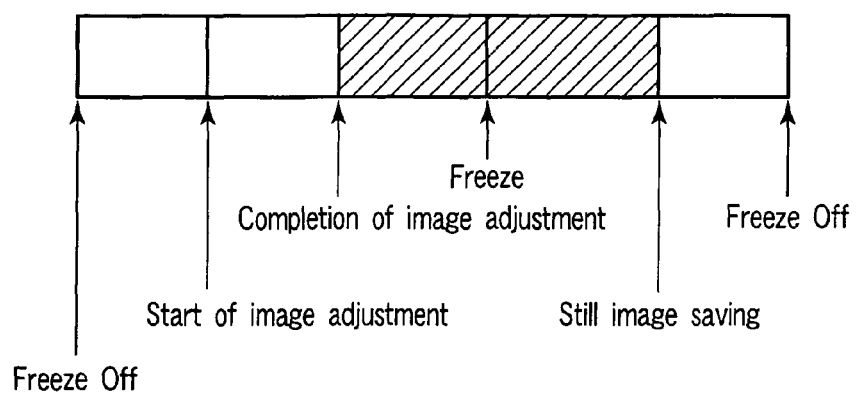
FIG. 10 is a view for explaining Example 7 of the ultrasonic diagnostic apparatus, in which the image recording start event is the final image adjustment operation, and the image recording end event is a still image saving operation.

FIG. 10 is a view for explaining Example 7 of the ultrasonic diagnostic apparatus. In this example, the image recording start event is the final image adjustment operation, and the image recording end event is a still image saving operation.

More specifically, an ultrasonic image saved as a still image is effective for diagnosis at a high probability. Hence, in this example, moving images during the period from a predetermined recording start event (final image adjustment operation in this example) to the saving instruction as a still image are formed as units and recorded in the image recording unit 28 as a series of moving image data.

Example 8

In this example, the image layout displayed on the monitor 14 is monitored. If the image layout is changed, an image recording start/end event signal is generated in accordance with the change as an event.

Figure 11:
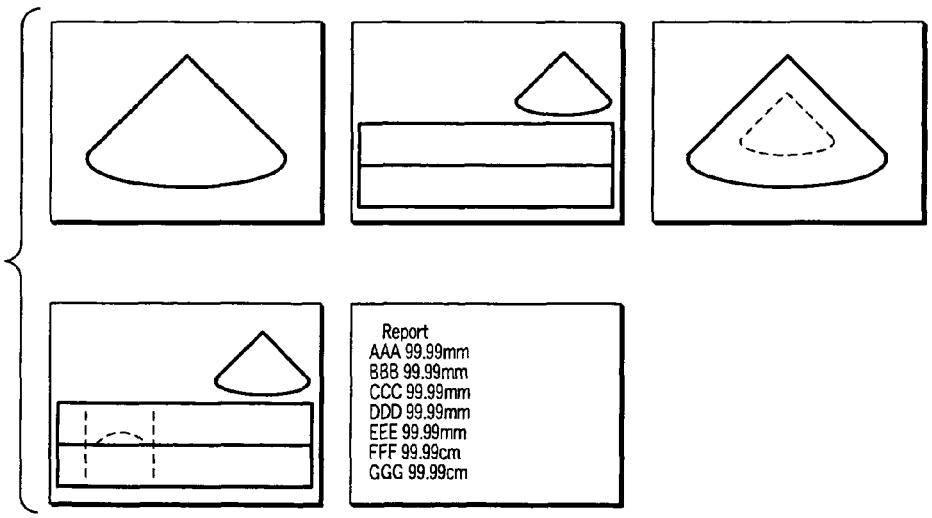
FIG. 11 is a view for explaining Example 8 of the ultrasonic diagnostic apparatus, in which when the image layout is changed, an image recording start/end event signal is generated in accordance with the change as an event.

FIG. 11 is a view for explaining Example 8 of the ultrasonic diagnostic apparatus. As shown in FIG. 11, on the monitor 14, an ultrasonic image, markers such as a scale marker, ROI marker, and zero Hz line marker (baseline), character information displayed at a specific position, Doppler sound (waveform), and the like are displayed by a predetermined image layout. When such various kinds of information are monitored, the current phase of imaging in the entire sequence can be determined.

More specifically, in, e.g., imaging in the Doppler mode, Doppler sound is collected. When the Doppler waveform is monitored, and the screen changes from a state without any Doppler waveform to a state with a Doppler waveform, it can be determined that imaging in the Doppler mode is started. On the other hand, when the screen changes from the state with a Doppler waveform to the state without any Doppler waveform, it can be determined that imaging in the Doppler mode is ended. Hence, ultrasonic images collected during the imaging period in the Doppler mode can also be recorded appropriately by using detection of a Doppler waveform as the image recording start event and disappearance of the Doppler waveform as the image recording end event.

When a Doppler waveform is displayed, the zero Hz line marker is displayed at a predetermined position. For this reason, the presence/absence of display of a Doppler waveform can be determined on the basis of the presence/absence of display of the zero Hz line marker. Hence, an event signal is generated in response to the start of display of the zero Hz line marker (i.e., the start of display of a Doppler waveform) to start image recording. An event signal is generated in response to the end of display of the zero Hz line marker (i.e., the end of display of the Doppler waveform) to end image recording.

Monitoring of the image layout has been described above. In imaging in the Doppler mode, Doppler sound is collected simultaneously. Hence, the image recording start/end event may be detection/disappearance of Doppler sound, not a change in image layout.

Example 9

In contrast echo using a contrast medium, the time phase when a large luminance change occurs is often effective for diagnosis because, e.g., the time phase corresponds to the contrast medium infusion timing. In this example, the luminance change of acquired ultrasonic images is compared between adjacent frames. If the change has a predetermined threshold value or more, an image recording start/end event signal is generated in response to the change as an event.

The threshold value serving as the reference for determination of the change is preferably arbitrarily set. The comparison target of luminance change may be a specific region such as an ROI. When TIC is to be created, the luminance change may be grasped by using it.

(Function of Acquiring/Setting Representative Image as Still Image)

The function of acquiring/setting a representative image as a still image, which is provided in the ultrasonic diagnostic apparatus 10, will be described. The representative image acquisition function generates an event signal in response to a specific event as a trigger, on the basis of the ultrasonic image data of a frame corresponding to the event signal generation, automatically generates a representative image (e.g., a thumbnail image) as a still image to be used as an index for search, and records the image in association with the ultrasonic image data of the corresponding frame. The representative image setting function reads out a recorded representative image, sets the image on the screen, and reproduces ultrasonic image data on the basis of the frame associated with the representative image selected by the operator. With this function, ultrasonic image data can be segmented into units and recorded on the basis of representative images. In addition, search of moving image data and search of a predetermined scene in each moving image data are facilitated.

FIG. 12 is a view for explaining processing by the representative image acquisition/setting function of the ultrasonic diagnostic apparatus 10. Referring to FIG. 12, the frame of the one-dot dashed line indicates representative image acquisition processing, and the frame of the two-dot dashed line indicates representative image setting processing.

Representative image acquisition processing will be described first. During image recording, when an event indicating representative image acquisition is activated, the control processor 27 generates an event signal and sends it to the recording control unit 26 (step S7). The recording control unit 26 checks whether the event signal indicates representative image acquisition (step S8). When the event signal is an event indicating representative image acquisition to "acquire, as a representative image, a frame image currently present on the frame memory", a representative image acquisition request is generated (step S9). In accordance with the representative image acquisition request, the authoring executes representative image acquisition processing (generation processing) on the basis of a frame image corresponding to event signal generation. The representative image is recorded in association with the corresponding frame image (step S10).

Representative image setting processing will be described next. To search for a desired scene (not always the scene at the start of recording) of a moving image after the end of image recording, the control processor 27 generates a signal to instruct a representative image setting request in response to an image by the operator and sends it to the recording control unit 26 (step S17). The recording control unit 26 transmits the representative image setting instruction to the authoring (step S18). The authoring executes setting processing of displaying a list of representative images in response to a predetermined instruction (step S19).

The contents of a predetermined event serving as a trigger in step S7 are not particularly limited. As in the image recording start/end event, an input operation or device operation unique to the ultrasonic diagnostic apparatus can be employed. Which input operation or device operation should be used as the representative image acquisition event is preferably arbitrarily registered.

Examples of the representative image acquisition/setting function of the ultrasonic diagnostic apparatus 10 will be described below by exemplifying an input operation or device operation used as a trigger. As in the recording start/recording end event, each representative image acquisition event is recorded as group information of a DICOM tab. The operator can also search for desired image data by using the recording start/recording end event as an index.

Example 10

Figure 13:
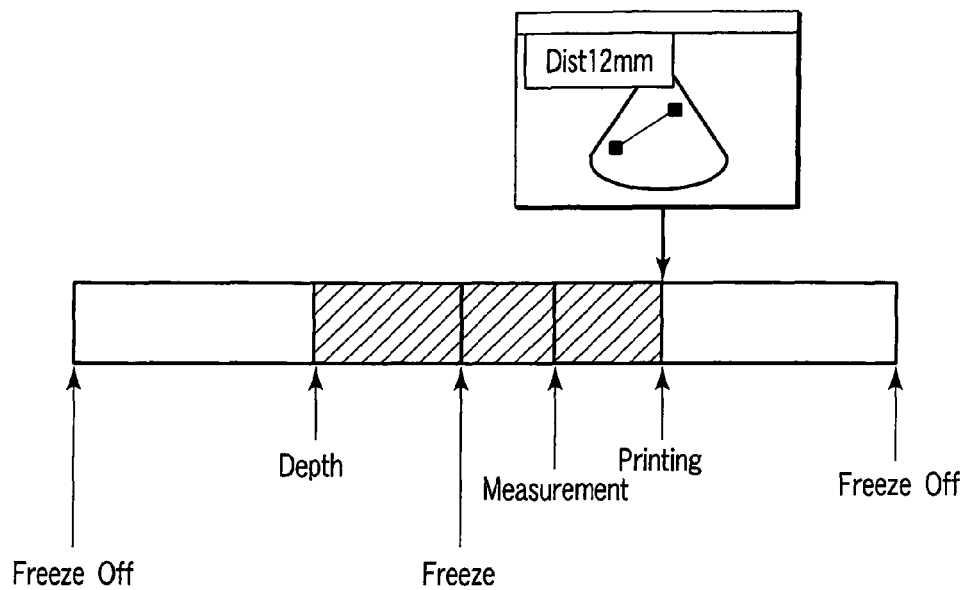
FIG. 13 is a view for explaining Example 10 of the ultrasonic diagnostic apparatus, in which a representative image is acquired in accordance with a print execution operation as a representative image acquisition event.

FIG. 13 is a view for explaining Example 10 of the ultrasonic diagnostic apparatus. An ultrasonic image printed in ultrasonic diagnosis is effective for diagnosis at a high probability. Hence, in this example, a print execution operation is used as the representative image acquisition event, and a representative image is acquired in response to this operation as a trigger, as shown in FIG. 13.

Example 11

Figure 14:
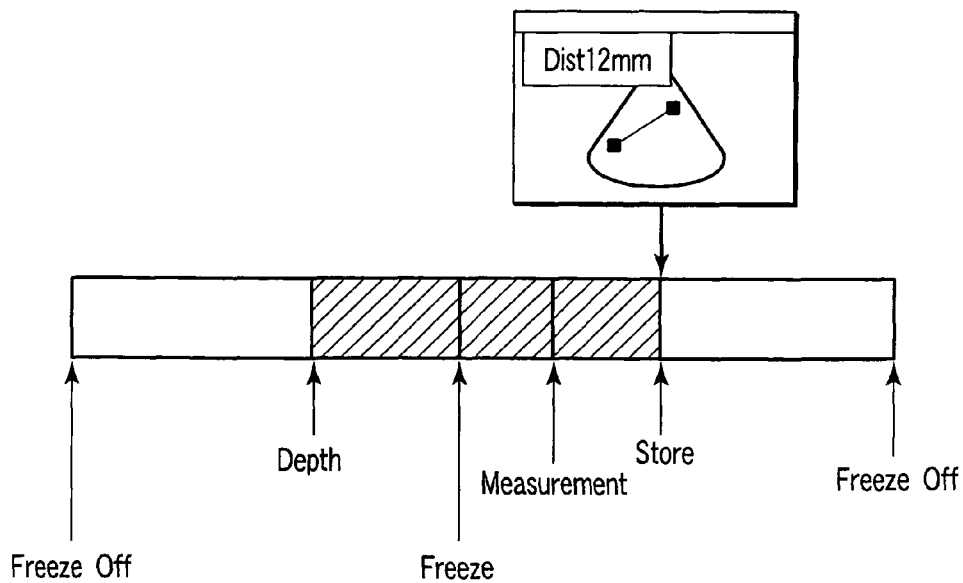
FIG. 14 is a view for explaining Example 11 of the ultrasonic diagnostic apparatus, in which a representative image is acquired in accordance with the still image saving operation as the representative image acquisition event.

FIG. 14 is a view for explaining Example 11 of the ultrasonic diagnostic apparatus. An ultrasonic image saved as a still image in ultrasonic diagnosis is effective for diagnosis at a high probability. Hence, in this example, a still image saving operation is used as the representative image acquisition event, and a representative image is acquired in response to this operation as a trigger, as shown in FIG. 14.

Example 12

Figure 15:
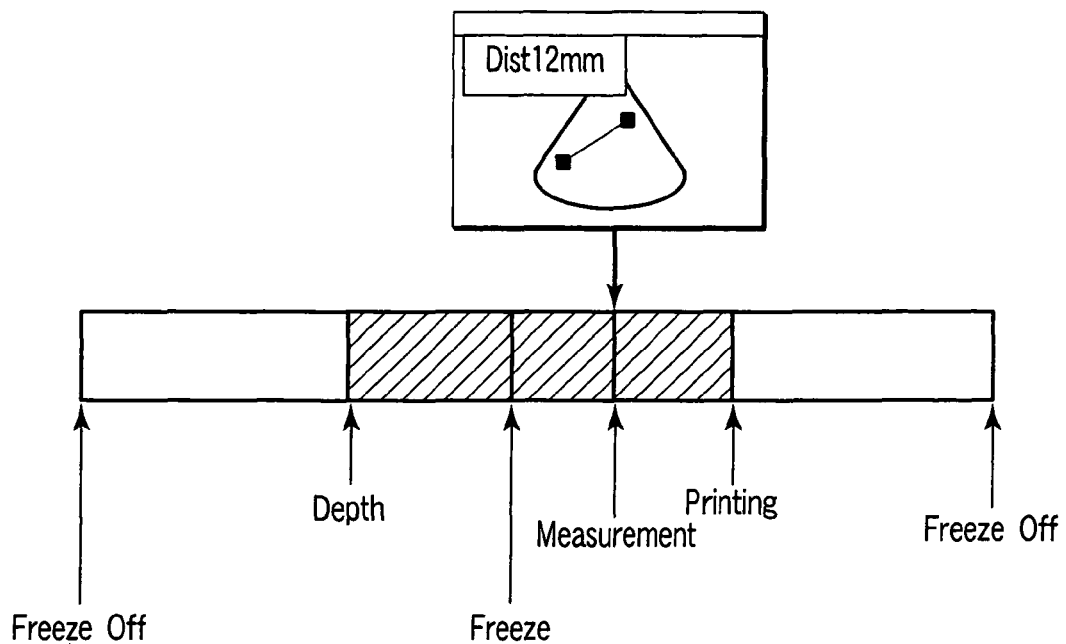
FIG. 15 is a view for explaining Example 12 of the ultrasonic diagnostic apparatus, in which a representative image is acquired in accordance with a measurement end operation as the representative image acquisition event.

FIG. 15 is a view for explaining Example 12 of the ultrasonic diagnostic apparatus. An ultrasonic image to be subjected to various kinds of measurements in ultrasonic diagnosis is effective for diagnosis at a high probability, as in Examples 10 and 11. Hence, in this example, a measurement end operation (or the final measurement end operation if a plurality of measurements are executed) is used as the representative image acquisition event, and a representative image is acquired in response to this operation as a trigger, as shown in FIG. 15.

Example 13

Figure 16:
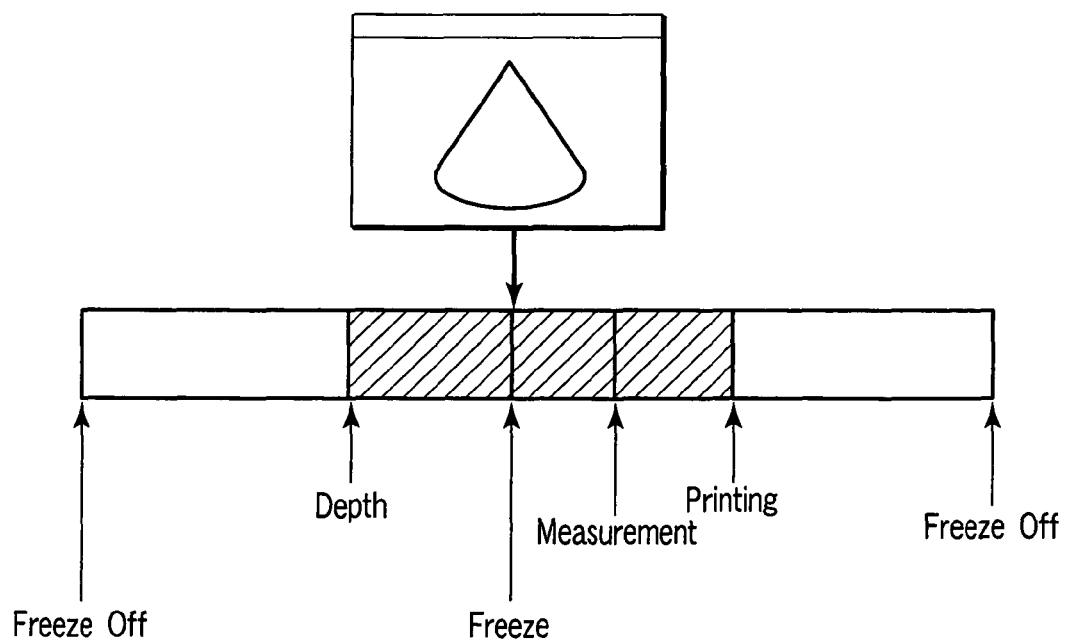
FIG. 16 is a view for explaining Example 13 of the ultrasonic diagnostic apparatus, in which a representative image is acquired in accordance with a freeze ON operation as the representative image acquisition event.

FIG. 16 is a view for explaining Example 13 of the ultrasonic diagnostic apparatus. An ultrasonic image to be subjected to freeze ON in ultrasonic diagnosis is effective for diagnosis at a high probability, as in Examples 10 to 12. Hence, in this example, a freeze ON operation is used as the representative image acquisition event, and a representative image is acquired in response to this operation as a trigger, as shown in FIG. 16.

Example 14

Figure 17:
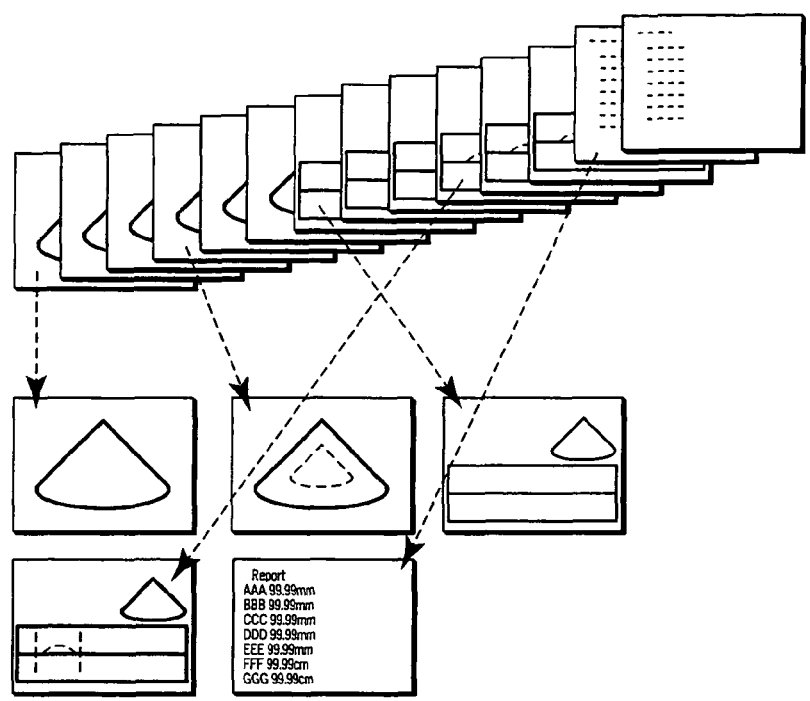
FIG. 17 is a view for explaining Example 14 of the ultrasonic diagnostic apparatus, in which a representative image is acquired in accordance with a change in image layout as the representative image acquisition event.
Figure 18:
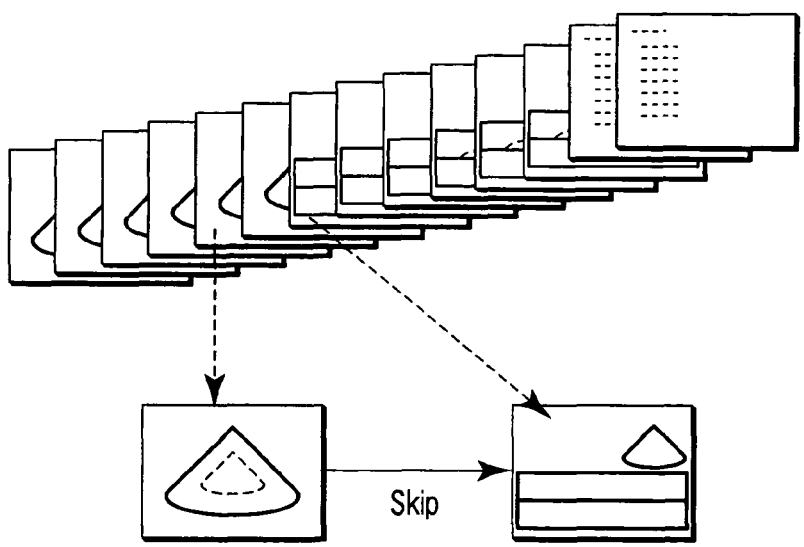
FIG. 18 is a view for explaining a modification to the embodiment.

In this example, the image layout is monitored, and a representative image is acquired in accordance with a change in image layout as the representative image acquisition event. FIG. 17 is a view for explaining Example 14 of the ultrasonic diagnostic apparatus. As shown in FIG. 17, when the image layout has changed in a series of imaging operations, the change is used as the representative image acquisition event, and an image (e.g., the first frame image immediately after the layout change) immediately after the change is acquired as a representative image. The representative image acquired in this example is not limited to the image immediately after the image layout change. For example, an image (e.g., the last frame image before the layout change) immediately before the change may be acquired.

The representative image acquisition method of this example does not always assume the above-described image recording function. For example, to reproduce a moving image recorded for a predetermined period, the moving image may be reproduced once as internal processing immediately before reproduction on the monitor 14 to monitor the image layout, and a representative image may be acquired.

(Function of Acquiring/Setting Representative Image as Moving Image)

The function of acquiring/setting a representative image (to be referred to as a representative moving image hereinafter) as a moving image, which is provided in the ultrasonic diagnostic apparatus 10, will be described next. The representative image acquisition function generates the above-described representative image as a moving image and records it in association with the ultrasonic image data of a corresponding frame. With this function, ultrasonic image data can be segmented into units and recorded on the basis of representative images. In addition, since a representative moving image to reproduce, e.g., an image of one heart beat is used as an index, search of moving image data and search of a predetermined scene in each moving image data are further facilitated.

Figure 19:
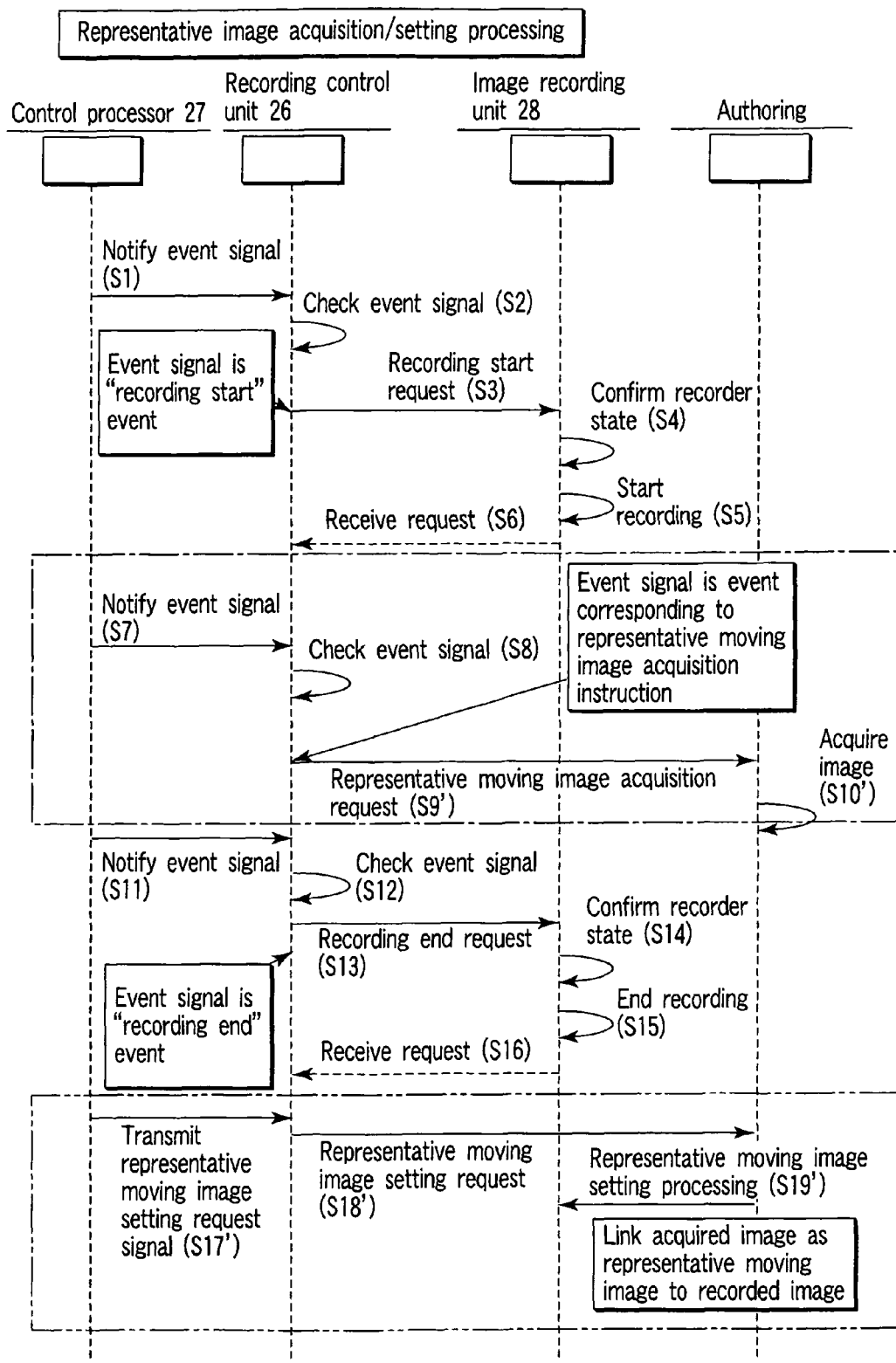
FIG. 19 is a view for explaining processing by the representative image acquisition/setting function of the ultrasonic diagnostic apparatus 10.

FIG. 19 is a view for explaining processing by the representative moving image acquisition/setting function of the ultrasonic diagnostic apparatus 10. The frame of the one-dot dashed line in FIG. 19 indicates representative moving image acquisition processing, and the frame of the two-dot dashed line indicates representative moving image setting processing. FIG. 19 is different from FIG. 12 in steps S9' and S10' of representative image acquisition processing and steps S17' to S19' of representative image setting processing. Processing in these steps will be described below.

The recording control unit 26 checks whether the event signal received from the control processor 27 indicates representative image acquisition (step S8). When the event signal is an event corresponding to a representative moving image acquisition instruction to "acquire, as a representative moving image, images corresponding to one heart beat from the current point", a representative image acquisition request is generated (step S9'). In accordance with this representative image acquisition request, the authoring executes representative moving image acquisition processing (generation processing) to acquire, as a representative moving image, images corresponding to one heart beat from the event signal generation time on the basis of a frame image corresponding to event signal generation. The representative moving image is recorded in association with the corresponding frame image (step S10'). The representative moving image generation corresponding to one heart beat from the event signal generation time is executed on the basis of, e.g., an ECG waveform acquired by an electrocardiograph (not shown).

As the event signal to instruct representative moving image acquisition, for example, one of Examples 10 to 14 described above can be employed. In this embodiment, a moving image corresponding to one heart beat from the event signal generation time is acquired as a representative moving image. However, the present invention is not limited to this. A moving image in any other period can be acquired if the image can serve as an index for search. The recording period and reproduction period of a representative moving image is preferably arbitrarily set.

In representative moving image setting processing, the control processor 27 sends a signal to instruct a representative moving image setting request to the recording control unit 26 (step S17'). The recording control unit 26 transmits the representative moving image setting instruction to the authoring (step S18'). The authoring executes setting processing of displaying a list of representative image images in response to a predetermined instruction (step S19'). When the operator selects a desired one of the representative images displayed as a list of moving images, moving image reproduction from, e.g., a frame image corresponding to the representative image can be executed.

According to the above-described arrangement, the following effects can be obtained.

According to this ultrasonic diagnostic apparatus, an operation or action unique to ultrasonic diagnosis is used as an image recording start event/image recording end event. The start/end of image recording is controlled on the basis of the operation or action as a trigger. Hence, recording of images unnecessary for diagnosis can be reduced as much as possible, and the finite recording area can effectively be used. In addition, no special operation for image recording by the operator is necessary, and image recording is always executed in accordance with a predetermined standard. Hence, highly objective diagnostic information can be provided easily and efficiently.

According to this ultrasonic diagnostic apparatus, since an operation or action unique to ultrasonic diagnosis is used as an image recording start event/image recording end event, moving images can be formed as units and managed by using an image recording start event/image recording end event as an index. Hence, even when a plurality of moving image data are recorded in the image recording unit, desired moving image data can be searched for quickly and easily by using the index.

In this ultrasonic diagnostic apparatus, when an operation or action unique to ultrasonic diagnosis is used as a representative image acquisition event, an arbitrary frame image in a moving image can be stored as a representative image. The representative images are displayed as a list in image search. When a desired corresponding image is selected, moving image reproduction from, e.g., a frame image corresponding to the representative image can be executed. Since image data can be formed as a unit and managed by using a representative image as an index, desired moving image data can be searched for quickly and easily.

When a representative image is created as a moving image, image data can be formed as a unit and managed by using a moving image corresponding to, e.g., one heart beat as an index. Hence, the contents of moving image data can be grasped more intuitively, and desired image data can be searched for quickly and easily by using the index.

Second Embodiment

The second embodiment of the present invention will be described next. An ultrasonic diagnostic apparatus according to this embodiment automatically forms and records units of moving image information based on a unified standard by using ultrasonic image data in a predetermined period, which is recorded together with event information containing the type and generation timing of an event signal.

FIG. 20 is a block diagram for explaining the arrangement of an ultrasonic diagnostic apparatus 10 according to this embodiment. FIG. 20 is different from FIG. 2 in that the apparatus further comprises an edited image storage unit 40.

An image recording unit 28 stores ultrasonic image data in a predetermined period, which is acquired in image diagnosis of a patient, together with event information about events which have occurred during the period. In this embodiment, under the control of a control processor 27, the image recording unit 28 stores ultrasonic image data (to be referred to as "whole period ultrasonic image data" hereinafter) which is acquired in a period (whole period) from the time when input (to be referred to as "new patient information input" hereinafter) is done in the ultrasonic diagnostic apparatus to instruct the start of image diagnosis for a new patient to the time when new patient information input for the next patient is done. In addition, event information about all events which have occurred during the period is stored. However, the present invention is not limited to these. Only event information about, e.g., an event selected in advance may be stored.

A recording control unit 26 executes editing processing (to be described later) for whole period ultrasonic image data on the basis of event information under the control of the control processor 27.

The edited image storage unit 40 stores the ultrasonic image data (to be referred to as "edited ultrasonic image data" hereinafter) edited by the recording control unit 26.

(Editing Function and Processing Using It)

The editing function provided in the ultrasonic diagnostic apparatus according to this embodiment will be described next. This function executes editing processing for whole period ultrasonic image data on the basis of event information stored in correspondence with the whole period ultrasonic image data, thereby automatically forming, as a unit, and recording moving image information after recording.

Figure 21:
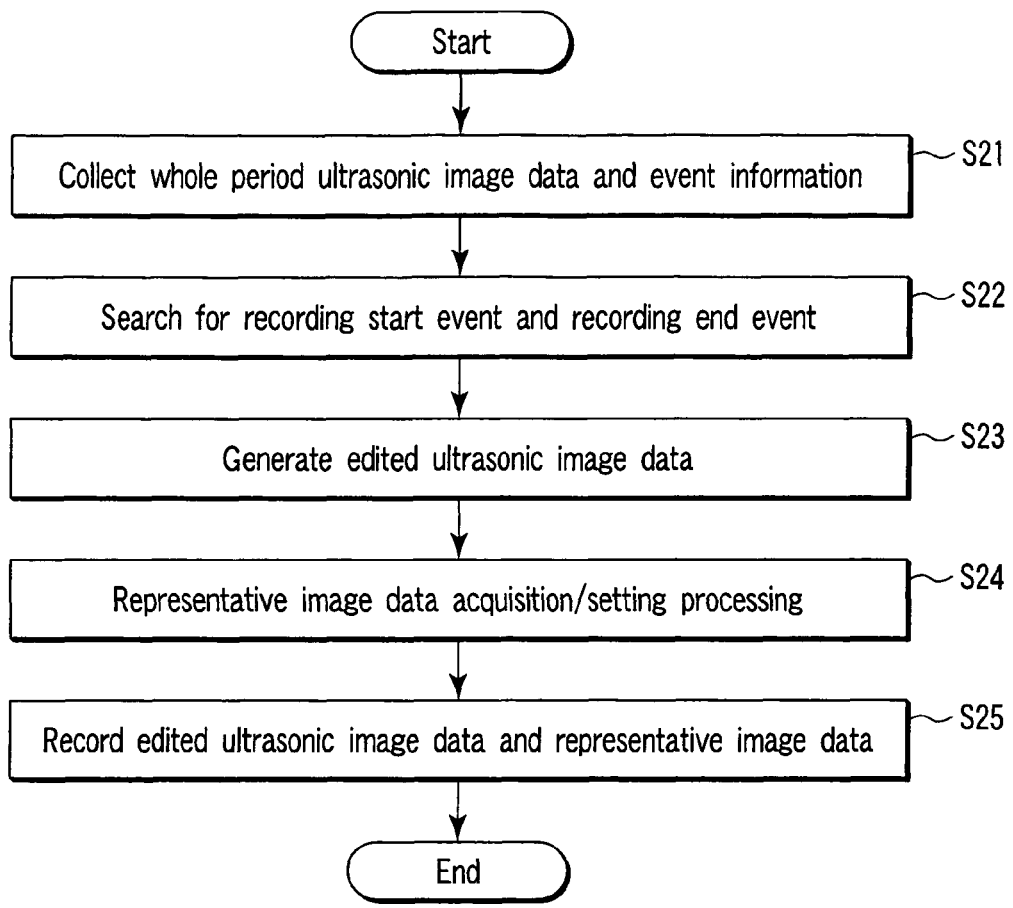
FIG. 21 is a flowchart showing the flow of processing of an editing function.

FIG. 21 is a flowchart showing the flow of processing of the editing function. Referring to FIG. 21, first, whole period ultrasonic image data and event information containing the types of event signals generated in the whole period and their timings are acquired and stored in the image recording unit 28 (step S21). When DICOM is used as an image communication standard, event information is recorded as group information of a DICOM tab.

The recording control unit 26 searches for a recording start event and recording end event from the event information stored in the image recording unit 28 (step S22). The recording control unit 26 generates edited ultrasonic image data by extracting a frame given a recording start event, a frame given a recording end event, and ultrasonic image data corresponding to frames between them (step S23).

The recording control unit 26 acquires and sets a representative image by using the found frame given the found event signal (step S24). This representative image can be either a still image or a moving image. The method of acquiring and setting the representative image is the same as that described in the first embodiment. The edited image storage unit 40 automatically stores the generated edited ultrasonic image data and representative image (step S25). The edited ultrasonic image data is linked to the representative image. Hence, when the operator selects a desired representative image, edited ultrasonic image data can be reproduced from an image corresponding to the representative image.

According to the above-described arrangement, edited ultrasonic image data is generated by using whole period ultrasonic image data and event information added to it. Hence, moving image information based on a unified standard can automatically be formed as a unit and recorded after recording. Processing can be done even in a medical workstation so that ultrasonic image editing can be easy and simple.

Note that the present invention is not exactly limited to the above embodiments, and constituent elements can be modified in the execution stage without departing from the spirit and scope of the invention. Detailed modifications are as follows.

(1) Each function according to the embodiments can be implemented even by installing a program to execute the processing in a computer such as a workstation and expanding the program on the memory. The program capable of causing the computer to execute the method may be stored in a recording medium such as a magnetic disk (e.g., a floppy disk or hard disk), optical disk (e.g., a CD-ROM or DVD), or semiconductor memory and distributed.

(2) According to the representative image setting function described in the above embodiments, when a representative image as an index is selected, a moving image which starts from, e.g., a recorded image linked to the representative image can be accessed at random. To quickly and easily access each section segmented by representative images, an interface such as a fast-forward button (rewind button) to skip reproduced images for each section may be provided.

(3) In the above embodiments, a stored ultrasonic image is reproduced on the basis of a frame associated with a selected representative image. The ultrasonic image reproduction form is not particularly limited. Detailed examples of the form are reproducing all ultrasonic images from a frame associated with a representative image, reproducing ultrasonic images corresponding to a predetermined period from (or before) a frame associated with a representative image, and reproducing ultrasonic images corresponding to a predetermined period before and after a frame associated with a representative image. The form is preferably selected by the operator arbitrarily.

Various inventions can be formed by properly combining a plurality of constituent elements disclosed in the above embodiments. For example, several constituent elements may be omitted from all the constituent elements described in the embodiments. In addition, constituent elements throughout different embodiments may be properly combined.

What is claimed is:

1. An ultrasonic diagnostic apparatus comprising:
   an ultrasonic probe which transmits an ultrasonic wave to a predetermined part of a subject and receives an echo signal from the predetermined part;
   a driving signal generation unit which generates a driving signal to drive the ultrasonic probe and supplies the driving signal to the ultrasonic probe;
   an image data generation unit which generates ultrasonic image data of a plurality of frames on the basis of the echo signal received by the ultrasonic probe;
   a control unit which registers at least one of an image adjustment operation, a predetermined measurement operation and an annotation operation as a specified event according to selection by a user;
   a recording unit which records the ultrasonic image data of each frame; and
   a signal generation unit which generates an event signal in response to an operation corresponding to the specified event,
   the control unit controlling at least one of a start and an end of recording of the ultrasonic image data by the recording unit in response to the event signal.

2. An apparatus according to claim 1, wherein the specified event is one of a change in image layout on a display screen on which an ultrasonic image data is displayed and a change by not less than a predetermined threshold value in luminance of the ultrasonic image data of each frame generated by the image data generation unit.

3. An apparatus according to claim 1, in which
   the recording unit records the specified event used as a trigger as supplementary information of the ultrasonic image data, and the apparatus further comprises a search unit which searches for desired data from the ultrasonic image data of each frame on the basis of the supplementary information.

4. An ultrasonic diagnostic apparatus comprising:
an ultrasonic probe which transmits an ultrasonic wave to a predetermined part of a subject and receives an echo signal from the predetermined part;
a driving signal generation unit which generates a driving signal to drive the ultrasonic probe and supplies the driving signal to the ultrasonic probe;
an image data generation unit which generates ultrasonic image data of a plurality of frames on the basis of the echo signal received by the ultrasonic probe;
a signal generation unit which generates an event signal in response to a predetermined event as a trigger;
a representative image generation unit which generates a representative image symbolically representing an ultrasonic image corresponding to the echo signal received in a period before or after event signal generation on the basis of the ultrasonic image data of a frame corresponding to an event signal generation timing;
a recording unit which records the ultrasonic image data of the plurality of frames and also records the representative image in association with the ultrasonic image data of the corresponding frame; and
an image reproduction unit which, when the representative image is selected, reproduces the ultrasonic image data on the basis of the frame associated with the selected representative image;
wherein the predetermined event is at least one of an image adjustment operation, an ultrasonic image print operation, a freeze ON/OFF operation, a predetermined measurement operation, an annotation operation, and a still image saving operation.

5. An apparatus according to claim 4, wherein the predetermined event is one of a change in image layout on a display screen on which an ultrasonic image data is displayed and a change by not less than a predetermined threshold value in luminance of the ultrasonic image data of each frame generated by the image data generation unit.

6. An apparatus according to claim 4, in which the recording unit records the predetermined event used as the trigger as supplementary information of the ultrasonic image data, and
the apparatus further comprises a search unit which searches for desired data from the ultrasonic image data of each frame on the basis of the supplementary information.

7. An apparatus according to claim 4, wherein the representative image is a still image using the ultrasonic image data of the frame corresponding to the event signal generation timing.

8. An apparatus according to claim 4, wherein the reproduction unit reproduces the ultrasonic image data corresponding to one of a frame associated with the selected representative image and a period after the frame, a frame associated with the selected representative image and a period before the frame, a predetermined period before and after a frame associated with the selected representative image.

9. An apparatus according to claim 4, wherein the representative image is a moving image containing the ultrasonic image data of the frame corresponding to the event signal generation timing.

10. An apparatus according to claim 9, wherein the representative image is a moving image corresponding to one heart beat period.

11. An ultrasonic diagnostic apparatus comprising:
an ultrasonic probe which transmits an ultrasonic wave to a predetermined part of a subject and receives an echo signal from the predetermined part;
a driving signal generation unit which generates a driving signal to drive the ultrasonic probe and supplies the driving signal to the ultrasonic probe;
an image data generation unit which generates ultrasonic image data of a plurality of frames on the basis of the echo signal received by the ultrasonic probe;
a signal generation unit which generates at least one of a first event signal to instruct one of a start and an end of image recording and a second event signal to instruct representative image acquisition in response to a predetermined event as a trigger;
a control unit which controls one of the start and the end of recording of the ultrasonic image data in response to the first event signal;
a representative image generation unit which generates a representative image symbolically representing an ultrasonic image corresponding to the echo signal received in a period before or after event signal generation on the basis of the ultrasonic image data of a frame corresponding to a second event signal generation timing;
a recording unit which records the ultrasonic image data of the plurality of frames and also records the representative image in association with the ultrasonic image data of the corresponding frame under control of the control unit; and
an image reproduction unit which, when the representative image is selected, reproduces the ultrasonic image data on the basis of the frame associated with the selected representative image,
wherein the predetermined event is at least one of an image adjustment operation, an ultrasonic image print operation, a freeze ON/OFF operation, a predetermined measurement operation, an annotation operation, and a still image saving operation.

12. An apparatus according to claim 11, wherein the predetermined event is at least one of an image adjustment operation and an ultrasonic image print operation.

13. An ultrasonic diagnostic apparatus comprising:
an image data generation unit which transmits an ultrasonic wave to a predetermined part of a subject and generates ultrasonic image data of a plurality of frames on the basis of an echo signal received from the predetermined part;
a signal generation unit which generates an event signal in response to a predetermined event as a trigger;
a recording unit which records the ultrasonic image data of each frame together with event information containing a type and generation timing of the event signal; and
an editing unit which edits the ultrasonic image data of the plurality of frames on the basis of the event information,
wherein the predetermined event is at least one of an image adjustment operation, an ultrasonic image print operation, a freeze ON/OFF operation, a predetermined measurement operation, an annotation operation, and a still image saving operation.

14. An apparatus according to claim 13, wherein the predetermined event is at least one of an image adjustment operation and an ultrasonic image print operation.

* * * * *